(12) United States Patent
Caccia

(10) Patent No.: US 9,555,239 B2
(45) Date of Patent: Jan. 31, 2017

(54) ELECTROPORATION APPLIANCE COMPRISING AN OBLONG APPLICATOR, RING ELECTRODES AND A SEAT FOR A SYRINGE

(71) Applicant: Giuseppe Caccia, Cassina Rizzardi (IT)

(72) Inventor: Giuseppe Caccia, Cassina Rizzardi (IT)

( * ) Notice: Subject to any disclaimer, the term of this patent is extended or adjusted under 35 U.S.C. 154(b) by 223 days.

(21) Appl. No.: 14/373,915

(22) PCT Filed: Jan. 30, 2013

(86) PCT No.: PCT/EP2013/000278
§ 371 (c)(1),
(2) Date: Jul. 23, 2014

(87) PCT Pub. No.: WO2013/117306
PCT Pub. Date: Aug. 15, 2013

(65) Prior Publication Data
US 2014/0350456 A1 Nov. 27, 2014

(30) Foreign Application Priority Data
Feb. 7, 2012 (IT) ................. CO2012A0004

(51) Int. Cl.
*A61N 1/32* (2006.01)
*A61N 1/05* (2006.01)
*A61N 1/04* (2006.01)
*A61M 31/00* (2006.01)

(52) U.S. Cl.
CPC .............. *A61N 1/327* (2013.01); *A61M 31/00* (2013.01); *A61N 1/0424* (2013.01); *A61N 1/0512* (2013.01); *A61N 1/0524* (2013.01)

(58) Field of Classification Search
CPC ........ A61N 1/327; A61N 1/32; A61N 1/0424; A61N 1/0512; A61N 1/0521; A61N 1/0524; A61M 31/00
See application file for complete search history.

(56) References Cited

U.S. PATENT DOCUMENTS

| | | | | |
|---|---|---|---|---|
| 4,881,526 A * | 11/1989 | Johnson | ................. | A61H 19/44 601/15 |
| 5,273,525 A * | 12/1993 | Hofmann | ............... | A61N 1/327 604/21 |
| 5,370,671 A * | 12/1994 | Maurer | ................ | A61N 1/0524 607/138 |
| 5,507,724 A * | 4/1996 | Hofmann | ............... | A61M 29/02 604/21 |
| 5,704,908 A * | 1/1998 | Hofmann | ............... | A61N 1/327 604/21 |
| 5,816,248 A * | 10/1998 | Anderson | ............ | A61N 1/0524 128/830 |

(Continued)

*Primary Examiner* — Andrew Gilbert
(74) *Attorney, Agent, or Firm* — Abelman, Frayne & Schwab

(57) ABSTRACT

A dynamic electroporation appliance comprises an oblong isolating applicator (1) with a rounded front part (4) and with two annular electrodes (3) arranged on its front surface at the sides of an intermediate opening (2). The intermediate opening it linked to at least one duct (9) associated with a central seat for a syringe (6) for dispensing pharmacological or aesthetic products or active ingredients. The electrodes (3) are energizable to produce a dynamic electroporation effect on the treated surface.

8 Claims, 1 Drawing Sheet

(56) References Cited

U.S. PATENT DOCUMENTS

Figure 1:
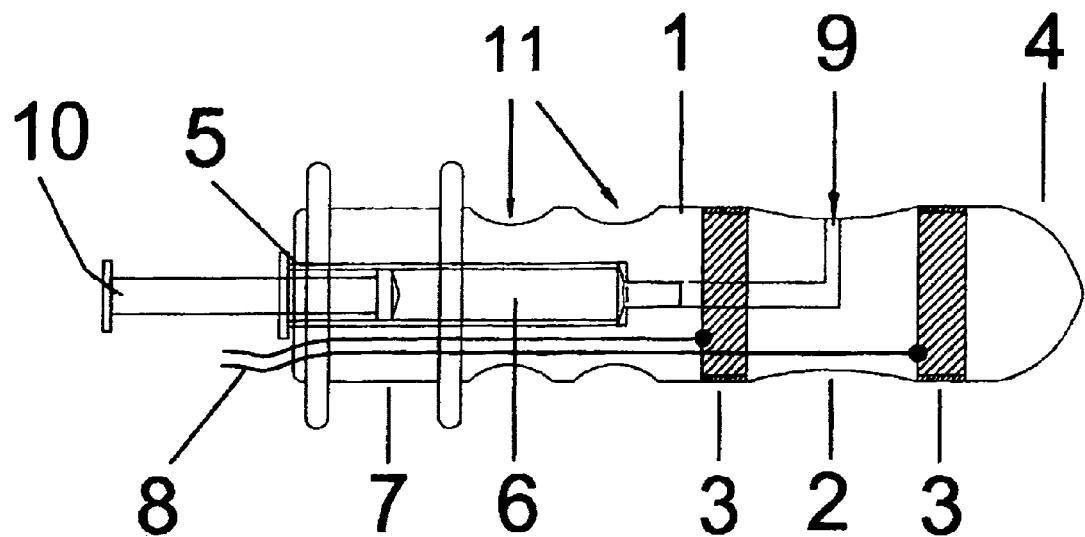

| | | | | |
|---|---|---|---|---|
| 7,125,394 B2* | 10/2006 | Berman | ............... | A61M 31/00 |
| | | | | 604/15 |
| 7,998,056 B2* | 8/2011 | Stifter | ................... | A61H 19/44 |
| | | | | 600/38 |
| 9,014,799 B2* | 4/2015 | Uhland | ................. | A61N 1/327 |
| | | | | 604/20 |
| 2011/0087155 A1* | 4/2011 | Uhland | ................. | A61N 1/327 |
| | | | | 604/21 |

* cited by examiner

ELECTROPORATION APPLIANCE COMPRISING AN OBLONG APPLICATOR, RING ELECTRODES AND A SEAT FOR A SYRINGE

RELATED APPLICATIONS

This application is a National Stage application of International Application PCT/EP/2013/000278 filed Jan. 30, 2013 and designating the U.S.A. and which claims priority of Italian Application No. CO2012A000004 filed Feb. 7, 2012, both applications being incorporated herein by reference thereto.

The invention refers to a dynamic electroporation appliance intended for the transdermal and/or transmucous vehiculation of fluid substances suitable for restoring normal vulvar and anal physiology.

It is currently known that to restore vaginal and/or anal aesthetic and/or pathological conditions, the necessary fluid medical products are applied on the surfaces to be treated or inserted in the vagina or in the anus, without being able to verify either the correct and uniform absorption by the inner tissues, especially in the case of applications of substances with high molecular weight, or the more or less effects caused by the mechanical actions that can occur through the use of needles and/or cannulas.

From U.S. Pat. No. 5,704,908 is known an electroporation appliance which comprises a catheter having an inflatable balloon for the introduction of medical substances into parts of the body; with such catheter however, the emission of the product occurs in an approximate way. This because the permeabilization and the consequent penetration of the applied product only occurs in correspondence to two areas opposite the balloon and not in the specific treatment area. Furthermore, with this catheter, it is hard to maintain a constant penetration depth due to the patient's muscle contractions consequent to the electroporation impulses.

In WO 2011/161474 is described an appliance for removing tissues from parts of a patient's body, as well as the related method.

The appliance can also be used to eliminate tissues as an alternative to laparotomy procedures, especially on weaker patients and comprises a number of electrodes that can be used to create a passage in the tissues for the catheter performing a therapeutic treatment.

US2011/245756 refers instead to a method for treating muscular disabilities.

Object of the present invention is to eliminate the above-mentioned drawbacks by means of a dynamic electroporation appliance characterised as indicated in the first claim. Other characteristics are the subject of the dependent claims.

A first advantage obtained by means of the present invention consists in the fact that the treatment develops according to a "dynamic" electroporation which, through the emission of electric impulses programmable in terms of frequency and amplitude, generates a transmembrane electric potential (e.g., from 0.5 to 1.5 V approx.), suitable for producing temporary impulses on the surfaces to be treated for modifying the state of the double lipid layer of the cellular membranes (and the subsequent return to natural conditions) with the consequent temporary formation of aqueous channels suitable for increasing, with respect to the current meagre or zero conditions, the permeability of the pharmaceutical products and/or fluid products required on a vaster variety of molecules.

Such temporary modifications are maintained in a "dynamic" state by means of said electric impulses, emitted at short predefined time intervals (e.g., a few milliseconds) and which have the function of ensuring the membranes have the chance to alternatively undergo partial dilations followed by the return to their state of balance.

Another advantage consists in the fact that creams and pharmaceutical products can be vehiculated deep down, without the use of needles and cannulas and without suffering for the users, acting directly on the cellular mechanisms otherwise out of reach, for the purpose of reactivating normal metabolic processes, regenerating new tissues and eliminating pathological ones.

More specifically, the dynamic electroporation appliance according to the invention permits:

vehiculating medical products and/or fluid aesthetic products, including non conductive, and including without the aid of conductive or non conductive gel, directly inside the vaginal and/or anal area, directly vehiculating active ingredients in pure state into the vaginal and/or anal areas, including liquid based, without the aid of gelling agents or solidifying agents, the carrying out of simple, quick and safe treatments, inside the vaginal and/or anal areas both in the medical and aesthetic fields, and also with self-application home interventions.

Substantially, the "dynamic" ion vehiculation produced in the above-mentioned way exploits the principle of electroporation, where the two electrodes are placed on the same applicator without the aid of the electric circuit closing plate, which acts on the internal vaginal and/or anal surfaces undergoing treatment, causing on these temporary elastic extensions which generate interstitial channels (electrophors) suitable for allowing a greater, uniform and deep, transdermal and transmucous vehiculation of the medical and/or aesthetic substances, including with high molecular weight.

Another advantage consists in the fact that the particular "compensated" wave shape of the electric impulses emitted does not produce electrolysis and, thanks to the particular frequencies used, the impulses manage to influence the cellular membrane undergoing treatment and to open the interstitial channels in much shorter times compared to iontophoresis devices.

Further advantages derive from the fact that the electric impulses stimulate:

the various receptors located underneath the skin; e.g., the Merkel corpuscles assigned to vascularization, favouring revascularization;

the supporting fibroblasts which produce new striae of collagen which retain water, essential for natural hydration; and the activity of the macrophages which "clean up the tissues".

Yet another advantage consists in the fact that such principle allows developing, effectively and without any contraindication, specific topical therapies for illnesses relating to:

degenerative processes tied to ageing, with important vascular complaints and cell atrophy, inflammatory processes secondary to sexually-transmitted illnesses (STI), cancer processes, inflammatory processes of the anus (haemorrhoids, prolapse, constipation).

the same appliance, by means of specific programmes, solves vaginal and anal incontinence problems.

Figure 2:
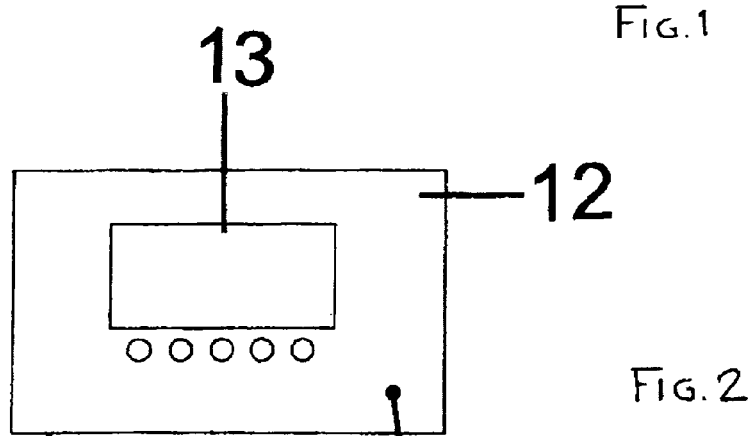

In point of fact, the present dynamic electroporation appliance consists of an applicator in non-conductive material, suitably profiled to permit easy and painless vaginal and/or anal introduction, wherein is included a central longitudinal housing for a standard syringe meant to contain and dispense fluid pharmacological, galenical or aesthetic products to be vehicled in the mucous such as:

hydrating or humidifying products for reducing or eliminating vaginal dryness, bio-generating and curative products such as: elastin, collagen, hyaluronic acid (which by retaining water increases turgidity), vitamins (A,E,F), antioxidants (coenzyme Q10), ascorbic acid and lipoic acid (with effects in the field of the cell matrix);

anti inflammatory substances;
analgesics;
muscle relaxants;
hormones (testosterone, oestrogens, progesterone);
anal decongestants;

The invention is described in detail below, according to one of its embodiments provided in an illustrative and non limitative way, with reference to the attached drawing wherein:

FIG. 1 represents a longitudinal section view of the vaginal and/or anal applicator of the dynamic electroporation appliance, and FIG. 2 schematically represents the appliance as a whole.

With reference to the illustrations, the appliance substantially consists of an applicator (1) in isolating material rounded in the front part (4) to favour an easy and painless introduction and adherence with the inner vaginal and/or anal wall to be treated. In the front intermediate part, besides the introductive area, the applicator comprises a partial convex area forming a substantially annular opening (2) at the sides of which are arranged two rings (3), in surgical steel or in conductive plastic material, electrically connected to the impulse generator.

In the rear part is a central seat (5) comprising a front coaxial duct with at least a radial drain (9) running into the substantially central area of said convex annular opening (2). In the seat (5) a syringe without needle (6) is positionable, with relative piston (10), designed to contain the pharmaceutical product, the aesthetic product or the active ingredient to be used. By means of the piston (10) the fluid product is pushed along the duct (9) and discharged in the convex annular opening (2) where it can expand and uniformly come into contact with the entire vaginal or anal surface to be treated, included between the electrodes (3) which, supplied by the electric impulse generator, perform the electroporation action needed to favour the uniform and deep transdermal and transmucous vehiculation of the medical substances, including with high molecular weight. In the rear part a grip (7) is provided designed to facilitate the introduction, the positioning, the emission action of the fluid products and the removal of the applicator.

Two circumferential convexes (11) arranged in the central part of the applicator (1) have the purpose of calibrating the introduction depth and make it easier to keep it in position, without supplementary manual supports.

In the rear part (7) of the applicator is also provided the exit of the connector or of the cables (8) for connecting the two electroporation electrodes (3) to a programmable command and control impulse generator (12) with display (13), powered by batteries or from the power mains (14).

The dynamic electroporation appliance is specifically usable for Gynaecological, Aesthetic and Functional applications and for Proctology, in particular and by way of example for: vaginal dryness; vulvar itching; dyspareunia; vulvar-vaginal burning sensation; hyperplastic, atrophic and mixed vulvar dystrophies; craurosi vulvare (lichen sclerosus); dyskeratosis; post-episiotomy scars; urinary incontinence; haemorrhoids; faecal incontinence.

The electroporation impulses produced by the appliance (12) supplying the applicator (1) are programmable in terms of frequency and amplitude depending on the many possible functions.

The invention claimed is:

1. A dynamic electroporation appliance, comprising an oblong applicator (1) in isolating material and having a rounded front part (4) for vaginal and/or anal introduction and an intermediate part adjoining the rounded front part; two ring electrodes (3) arranged on the front part in a spaced relationship to each other; an impulse generator (12) with programmable voltage and frequency and formed as a command and control generator, said two ring electrodes (3) being connected to said impulse generator (12); a duct extending through a seat (5) provided in a rear part of the applicator and connected with an opening (2) provided in the front part between said two ring electrodes (3); and a needless syringe (6) supported on the seat (5) and having a piston (10), said syringe operating as a manual dispenser of pharmacological or aesthetic products or active ingredients, wherein said impulse generator (12) is powered by batteries or mains (14) and supply impulse electric voltage to said two ring electrodes (3); and wherein said duct is connected with said opening (2) by a radial drain (9), and said opening (2) defining a partial convex discharge area between said two ring electrodes (3) through which a respective product supplied through the radial drain (9) is discharged against a to-be-treatable vaginal or anal surface.

2. The dynamic electroporation appliance according to claim 1, wherein said two ring electrodes are in conductive surgical steel.

3. The dynamic electroporation appliance according to claim 1, wherein said two ring electrodes are in conductive plastic material.

4. The dynamic electroporation appliance according to claim 1, wherein said two ring electrodes are positioned on the applicator for transmitting programmable, in terms of frequency and amplitude, impulses generated by said impulse generator.

5. The dynamic electroporation appliance according to claim 1, wherein said impulse generator produces electrical impulses in short time intervals predefined or adjustable from a display.

6. The dynamic electroporation appliance according to claim 1, wherein a grip (7) is provided in the rear part of the applicator for vaginal or anal introduction of the applicator, emission action of pharmacological or aesthetic products, and withdrawal of the applicator.

7. The dynamic electroporation appliance according to claim 1, wherein at least two circumferential convexes (11) are provided in a central part located between the front and rear parts for calibrating a vaginal or anal introduction depth and for retaining the applicator in a predetermined position, without manual support.

8. The dynamic electroporation appliance according to claim 1, wherein a connector or cables (8) which connect said two ring electrodes (3) with the pulse generator (12) extend through the rear part of the applicator.

* * * * *